US011440857B2

(12) United States Patent
Khawaji et al.

(10) Patent No.: US 11,440,857 B2
(45) Date of Patent: Sep. 13, 2022

(54) CATALYST SYSTEMS

(71) Applicant: Saudi Arabian Oil Company, Dhahran (SA)

(72) Inventors: Motaz Khawaji, Thuwal (SA); Sohel Shaikh, Dhahran (SA); Wei Xu, Thuwal (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/537,627

(22) Filed: Nov. 30, 2021

(65) Prior Publication Data

US 2022/0169583 A1 Jun. 2, 2022

Related U.S. Application Data

(60) Provisional application No. 63/119,221, filed on Nov. 30, 2020, provisional application No. 63/119,142, filed on Nov. 30, 2020, provisional application No. 63/119,206, filed on Nov. 30, 2020, provisional application No. 63/119,141, filed on Nov. 30, 2020, provisional application No. 63/119,217, filed on Nov. 30, 2020.

(51) Int. Cl.
*C07C 2/36* (2006.01)
*B01J 31/22* (2006.01)
*B01J 31/24* (2006.01)

(52) U.S. Cl.
CPC .............. *C07C 2/36* (2013.01); *B01J 31/2213* (2013.01); *B01J 31/2409* (2013.01); *B01J 2231/20* (2013.01); *B01J 2531/31* (2013.01); *B01J 2531/62* (2013.01); *C07C 2531/14* (2013.01); *C07C 2531/24* (2013.01)

(58) Field of Classification Search
CPC ... C07C 2/36; C07C 2531/14; C07C 2531/24; C07C 2531/26; B01J 31/2213; B01J 31/2409; B01J 2231/20; B01J 2531/31; B01J 2531/62; B01J 31/0231; B01J 31/0239; B01J 31/188; B01J 31/0209; B01J 31/143
See application file for complete search history.

(56) References Cited

U.S. PATENT DOCUMENTS

| | | | |
|---|---|---|---|
| 2,738,151 A | 3/1956 | Herzog | |
| 3,061,602 A | 10/1962 | Duck et al. | |
| 3,686,350 A | 8/1972 | Yamada et al. | |
| 4,242,531 A | 12/1980 | Carter | |
| 4,484,016 A | 11/1984 | Maschmeyer et al. | |
| 4,528,415 A | 7/1985 | Knudsen | |
| 4,532,370 A | 7/1985 | Le Quan et al. | |
| 4,538,018 A | 8/1985 | Carter | |
| 4,606,854 A | 8/1986 | Ozawa et al. | |
| 4,615,998 A | 10/1986 | Le Quan et al. | |
| 5,292,837 A | 3/1994 | Heinrich et al. | |
| 5,376,706 A | 12/1994 | Barsotti et al. | |
| 5,494,171 A | 2/1996 | Kazamoto et al. | |
| 5,728,912 A | 3/1998 | Saqualain Haider Rizvi et al. | |
| 5,792,895 A | 8/1998 | Commereuc et al. | |
| 5,811,618 A | 9/1998 | Wu | |
| 5,856,612 A | 1/1999 | Araki et al. | |
| 5,877,376 A | 3/1999 | Commereuc et al. | |
| 6,147,172 A * | 11/2000 | Brown .................... C08F 10/00 502/103 |
| 6,184,428 B1 | 2/2001 | Zahoor et al. | |
| 6,239,061 B1 * | 5/2001 | Wang ..................... C08F 10/02 556/14 |
| 6,710,005 B1 * | 3/2004 | Guo ....................... B01J 31/143 502/103 |

(Continued)

FOREIGN PATENT DOCUMENTS

| CN | 101189270 A | 5/2008 |
|---|---|---|
| CN | 102807632 A | 12/2012 |

(Continued)

OTHER PUBLICATIONS

International Search Report and Written Opinion dated Feb. 28, 2022 pertaining to International application No. PCT/US2021/060330 filed Nov. 22, 2021, 17 pages.
International Search Report and Written Opinion dated Mar. 1, 2022 pertaining to International application No. PCT/US2021/061115 filed Nov. 30, 2021, 20 pages.
International Search Report and Written Opinion dated Mar. 4, 2022 pertaining to International application No. PCT/US2021/061114 filed Nov. 30, 2021, 20 pages.
International Search Report and Written Opinion dated Mar. 4, 2022 pertaining to International application No. PCT/US2021/061116 filed Nov. 30, 2021, 20 pages.
Tao, Jiang et al., "A series of novel bisphosphinoamine ligands: Synthesis, characterization and application in ethylene tetramerization", Chinese Science Bulletin, Science China Press (SCP) and Springer, CN, vol. 55, No. 33, Nov. 1, 2010, pp. 3750-3754.

(Continued)

*Primary Examiner* — Ali Z Fadhel
(74) *Attorney, Agent, or Firm* — Dinsmore & Shohl LLP

(57) ABSTRACT

Catalyst systems suitable for tetramerizing ethylene to form 1-octene may include a catalyst including a reaction product of a chromium compound and a ligand having the structure according to Formula (II). In Formula (II), A and C may be independently chosen from phosphorus, arsenic, antimony, bismuth, and nitrogen; B may be a linking group between A and C; and $R_1$, $R_2$, $R_3$, and $R_4$ may be independently chosen from a $(C_1-C_{50})$ hydrocarbyl or a $(C_1-C_{50})$ heterohydrocarbyl. The catalyst system may include a co-catalyst including a reaction product of an organoaluminum compound and an antifouling compound. The antifouling compound may include one or more quaternary salts; one or more organic acids, organic acid salts, esters, anhydrides, or combinations of these; one or more chlorinated hydrocarbons, chloroaluminum alkyls, or combinations of these; one or more polyether alcohols; or one or more non-polymeric ethers.

19 Claims, No Drawings

(56) References Cited

U.S. PATENT DOCUMENTS

| | | |
|---|---|---|
| 6,767,975 B1 | 7/2004 | Liu |
| 6,903,042 B2 | 6/2005 | Drochon et al. |
| 7,122,497 B1 | 10/2006 | Nagy et al. |
| 7,157,532 B2 | 1/2007 | Payer et al. |
| 7,297,832 B2 | 11/2007 | Blann et al. |
| 7,300,904 B2 | 11/2007 | Dixon et al. |
| 7,329,635 B2 | 2/2008 | Dickakian et al. |
| 7,361,623 B2 | 4/2008 | Dixon et al. |
| 7,638,597 B2 | 12/2009 | Etherton et al. |
| 7,919,569 B2 | 4/2011 | Xu et al. |
| 7,964,763 B2 | 6/2011 | Dixon et al. |
| 8,227,653 B2 | 7/2012 | Weber et al. |
| 8,252,871 B2 | 8/2012 | Aliyev et al. |
| 10,280,125 B2 | 5/2019 | Sogo et al. |
| 10,471,416 B2 | 11/2019 | Im et al. |
| 11,104,621 B2 | 8/2021 | Khawaji et al. |
| 2003/0109766 A1 | 6/2003 | Commereuc et al. |
| 2004/0259720 A1 | 12/2004 | Sato et al. |
| 2005/0288470 A1 | 12/2005 | Benham et al. |
| 2007/0027276 A1 | 2/2007 | Cann et al. |
| 2009/0105488 A1 | 4/2009 | Cheng et al. |
| 2010/0113257 A1 | 5/2010 | Kreishcher et al. |
| 2010/0190939 A1 | 7/2010 | Fritz et al. |
| 2010/0274065 A1 | 10/2010 | Sydora |
| 2012/0029258 A1 | 2/2012 | Al-Masned et al. |
| 2012/0172645 A1 | 7/2012 | Sydora |
| 2013/0123443 A1 | 5/2013 | Siraux et al. |
| 2013/0303817 A1 | 11/2013 | Shaik et al. |
| 2014/0088331 A1 | 3/2014 | Rolland |
| 2014/0250835 A1 | 9/2014 | Prabhu et al. |
| 2015/0087873 A1 | 3/2015 | Overett et al. |
| 2015/0141605 A1 | 5/2015 | Bradin |
| 2016/0122371 A1 | 5/2016 | Lee et al. |
| 2016/0311950 A1 | 10/2016 | Batinas-Geurts et al. |
| 2016/0367977 A1* | 12/2016 | Shaikh ............. B01J 31/04 |
| 2017/0197892 A1* | 7/2017 | Khawaji ............. C07C 2/32 |
| 2017/0274356 A1 | 9/2017 | Cann et al. |
| 2018/0327332 A1* | 11/2018 | Sogo ............. C07C 2/32 |
| 2019/0092707 A1* | 3/2019 | Melibari ............. C07C 2/30 |
| 2019/0092709 A1* | 3/2019 | Bischof ............. B01J 31/2438 |
| 2019/0308179 A1 | 10/2019 | Lee et al. |

FOREIGN PATENT DOCUMENTS

| | | |
|---|---|---|
| CN | 103665201 A | 3/2014 |
| CN | 103724149 A | 4/2014 |
| CN | 107778388 A | 3/2018 |
| EP | 0135441 A1 | 3/1985 |
| EP | 0181954 A1 | 5/1986 |
| EP | 0221206 A1 | 5/1987 |
| EP | 0352856 A1 | 1/1990 |
| EP | 2738151 A1 | 6/2014 |
| EP | 3536696 A1 | 9/2019 |
| EP | 3640232 A1 | 4/2020 |
| EP | 3805240 A1 | 4/2021 |
| JP | H0288529 A | 3/1990 |
| RU | 2561921 C1 | 9/2015 |
| WO | 2010092554 A1 | 8/2010 |
| WO | 2012013805 A1 | 2/2012 |
| WO | 2013154446 A1 | 10/2013 |
| WO | 2013168106 A1 | 11/2013 |
| WO | 2015087303 A2 | 6/2015 |
| WO | 2015087304 A2 | 6/2015 |
| WO | 2015087305 A2 | 6/2015 |
| WO | 2015118462 A1 | 8/2015 |
| WO | 2017120310 A1 | 7/2017 |
| WO | 2018106764 A1 | 6/2018 |
| WO | 2019235799 A1 | 12/2019 |

OTHER PUBLICATIONS

Database CA [Online] Chemical Abstracts Service, Columbus, Ohio, US; 2014, Sun, Yueming et al "Boron- and silicon-bridged bis(diphenylphosphino)-type ligands for chromium-catalyzed ethylene oligomerization", XP002805681, retrieved from STN Database accession No. 2014:525027 abstract & Sun, Yueming et al: "Boron-and silicon-bridged bis(diphenylphosphino)-type ligands for chromium-catalyzed ethylene oligomerization" Chinese Science Bulletin, 59(21), 2613-2617; ISSN: 1001-6538, 2014.

Baojun, Zhang et al., "Cr(III)-Based Catalyst System for Oligomerization of Ethylene to 1-Octene with High Selectivity", Chinese Journal of Catalysis, vol. 28, No. 4, Jan. 1, 2007, pp. 317-320.

Chen, Hongxia et al., "Effects of halide in homogeneous Cr(III)/PNP/MAO catalytic systems for ethylene etramerization toward 1-octene", Journal of Molecular Catalysis A: Chemical, Elsevier, Amsterdam, NL, vol. 270, No. 1-2, May 7, 2007, pp. 273-277.

AiJaralla et al. "Dimerization of Ethylene to Butene-1" Catalysis Today, 14 (1992) 1-124, 121 pgs.

Bariashier et al. "Recent advances in homogeneous chromium catalyst design for ethylene tri-, tetra-, oligo- and polymerization" Coordination Chemistry Reviews 385 (2019) 208-229, 22 pgs.

Bartlett et al. "Triptycene (9,10-o-Benzenoanthracene)" Contribution from the Converse Memorial Laboratory of Harvard University, Nov. 1942, 5 pgs.

Blann et al. "Ethylene tetramerisation: Subtle effects exhibited by N-substituted diphosphinoamine ligands" Journal of Catalysis 249 (2007) 244-249, 6 pgs.

Bollmann et al. "Ethylene Tetramerization: A New Route to Produce 1-Octene in Exceptionally High Selectivities" J. Am. Chem. Soc. 2004, 126, 2 pgs.

Elowe et al. "Nitrogen-Linked Diphosphine Ligands with Ethers Attached to Nitrogen for Chromium Catalyzed Ethylene Tri- and Tetramerizations" Arnold and Mabel Beckman Laboratories of Chemical Synthesis, 8 pgs.

Farrell "Developments in Linear Alpha Olefin (LAO) Comonomer Technologies for Polyethylene" Chemsystems PERP 2011S11, May 2012, 7 pgs.

Fei et al. "Influence of the functional group on the synthesis of aminophosphines, diphosphinoamines and iminobiphosphines" Dalton Trans., 2003, 2772-2779, 8 pgs.

Forestiere et al. "Oligomerization of Monoolefines by Homgeneous Catalysts" Oil & Gas Science and Technology—Rev. IFP, vol. 64 (2009) No. 6, 19 pgs.

Hennico "Butene-1 is made from ethylene" Hydrocarbon Processing, Journal vol. 69:3, 1990, Abstract Only, 2 pgs.

Karin et al. "Removal of Trace Elemental Impurities from Polyethylene by Nitric Acid" Analytical Chemistry, vol. 47, No. 13, Nov. 1975, 4 pgs.

Killian et al. "The use of bis(diphenylphosphino)amines with N-aryl functionalities in selective ethylene tri- and tetramerisation" Journal of Molecular Catalysis A: Chemical 270 (2007) 214-218, 5 pgs.

Kim et al. "Ligand Modification for Selectivity Control in Selective Ethylene Oligomerization" Macromol. Res., 26(4), 341-345 (2018), 5 pgs.

Kim et al. "MAO-free and extremely active catalytic system for ethylene tetramerization" Appl Organometal Chem. 2019;33:e4829, 13 pgs.

Mole "Organoaluminium Compounds" Aust. J. Chem., 1966, 19, 381-6, 6 pgs.

Obrey et al. "A Lewis Base Promoted Alkyl/Alkoxide Ligand Redistribution: Reaction of [Me2Al(u-OCPh3)]2 with THF" Organometallics 2001, 20, 5119-5124, 6 pgs.

Pietrzykowski et al. "Reactions of methyl- and ethylaluminium compounds with alkoxyalcohols. The influence of alkoxyalchohol substituents on the structure of the complexes formed" Inorganica Chimica Acta 334 (2002) 385-394, 10 pgs.

Smith et al. "Ethylene Dimerization over Supported Titanium Alkoxides" Journal of Catalysis 105, 187-198 (1987), 12 pgs.

Sydora "Selective Ethylene Oligomerization" Organometallics 2019, 38, 997-1010, 14 pgs.

Weidman et al. "Triptycene-based copolyimides with tailored backbone rigidity for enhanced gas transport" Polymer 126(2017) 314-232, 10 pgs.

Chinese First Office Action dated Nov. 6, 2019, pertaining to Chinese Patent Application No. 201680035981.0.

(56) References Cited

OTHER PUBLICATIONS

European Extended Search Report dated Dec. 20, 2019, pertaining to European Patent Application No. 19188473.3.
India Examination Report dated Apr. 27, 2020, pertaining to Indian Patent Application No. 201837025980.
Translation of Japanese Office Action dated Jul. 8, 2020, pertaining to Japanese Patent Application No. 2017-565808.
Translation of Japanese Office Action dated Jan. 6, 2021, pertaining to Japanese Patent Application No. 2018-535418.
Translation of Russian Office Action dated Feb. 27, 2020, pertaining to Russian Patent Application No. 2018128919.
Final Office Action dated Feb. 25, 2021, pertaining to U.S. Appl. No. 15/181,923.
Final Office Action dated May 10, 2019, pertaining to U.S. Appl. No. 15/181,923.
Non-Final Office Action dated Aug. 20, 2020, pertaining to U.S. Appl. No. 15/181,923.
Non-Final Office Action dated Sep. 4, 2019, pertaining to U.S. Appl. No. 15/181,923.
Non-Final Office Action dated Dec. 13, 2018, pertaining to U.S. Appl. No. 15/181,923.
Invitation to Pay Additional Fees dated Sep. 15, 2016, pertaining to Int'l Patent Application No. PCT/US2016/037366.
International Search Report and Written Opinion dated Nov. 21, 2016, pertaining to Int'l Patent Application No. PCT/US2016/037366.
Final Office Action dated Feb. 28, 2020, pertaining to U.S. Appl. No. 15/393,865.
Final Office Action dated Aug. 10, 2018, pertaining to U.S. Appl. No. 15/393,865.
Notice of Allowance and Fees Due dated Apr. 28, 2021, pertaining to U.S. Appl. No. 15/393,865.
Non-Final Office Action dated Jan. 4, 2021, pertaining to U.S. Appl. No. 15/393,865.
Non-Final Office Action dated Jan. 11, 2019, pertaining to U.S. Appl. No. 15/393,865.
Non-Final Office Action dated Mar. 13, 2018, pertaining to U.S. Appl. No. 15/393,865.
International Search Report and Written Opinion dated Jun. 8, 2017, pertaining to Int'l Patent Application No. PCT/US2017/012299.
Non-Final Office Action dated Oct. 19, 2018, pertaining to U.S. Appl. No. 15/830,800.
International Search Report and Written Opinion dated Feb. 20, 2018, pertaining to Int'l Patent Application No. PCT/US2017/064841.
Notice of Allowance and Fees due dated Sep. 10, 2020, pertaining to U.S. Appl. No. 16/134,207.
Non-Final Office Action dated Mar. 30, 2020, pertaining to U.S. Appl. No. 16/134,207.
International Search Report and Written Opinion dated Jan. 3, 2019, pertaining to Int'l Patent Application No. PCT/US2018/051514.
International Search Report and Written Opinion dated Mar. 18, 2021, pertaining to Int'l Patent Application No. PCT/US2020/059974.
Singapore Office Action dated Aug. 10, 2020, pertaining to Singapore Patent Application No. 11201805653U.
Notification of Transmittal of the International Search Report and the Written Opinion of the International Searching Authority, or the Declaration dated Mar. 15, 2022 pertaining to International application No. PCT/US2021/061123 filed Nov. 30, 2021, 20 pages.
Notification of Transmittal of the International Search Report and the Written Opinion of the International Searching Authority, or the Declaration dated Mar. 11, 2022 pertaining to International application No. PCT/US2021/061117 filed Nov. 30, 2021, 23 pages.
Kim, Eun Ho et al. "Methylaluminoxane-Free Chromium Catalytic System for Ethylene Tetramerization", ACS OMEGA, vol. 2, No. 3, Mar. 31, 2017, pp. 765-773.
Wang, Tao et al. "Mixed aluminoxanes: efficient cocatalysts for bisphosphineamine/Cr(III) catalyzed ethylene tetramerization toward 1-octene", Applied Petrochemical Research, vol. 5, No. 2, Mar. 1, 2015, pp. 143-149.

\* cited by examiner

CATALYST SYSTEMS

CROSS REFERENCE TO RELATED APPLICATIONS

This application claims the benefit of and priority to U.S. Application Ser. No. 63/119,141 filed on Nov. 30, 2020 and entitled "Catalyst Systems," the entire contents of which are incorporated by reference in the present disclosure. Additionally, this application claims the benefit of and priority to U.S. Application Ser. No. 63/119,142 filed on Nov. 30, 2020 and entitled "Catalyst Systems," the entire contents of which are incorporated by reference in the present disclosure. Additionally, this application claims the benefit of and priority to U.S. Application Ser. No. 63/119,206 filed on Nov. 30, 2020 and entitled "Catalyst Systems," the entire contents of which are incorporated by reference in the present disclosure. Additionally, this application claims the benefit of and priority to U.S. Application Ser. No. 63/119,217 filed on Nov. 30, 2020 and entitled "Catalyst Systems," the entire contents of which are incorporated by reference in the present disclosure. Additionally, this application claims the benefit of and priority to U.S. Application Ser. No. 63/119,221 filed on Nov. 30, 2020 and entitled "Catalyst Systems," the entire contents of which are incorporated by reference in the present disclosure.

TECHNICAL FIELD

Embodiments of the present disclosure generally relate chemical processing and, more particularly, to catalyst systems utilized in such chemical processing.

BACKGROUND

Linear alpha-olefins ("LAOs") were historically produced from cracking of refinery products or products of non-selective oligomerization of ethylene as a broad olefin fraction. Demand for these compounds is rising in North America, Western Europe, and Asia. Currently, there are several industrial processes that produce LAOS. Notably, the Shell Higher Olefin Process (SHOP), which has been in operation since 1977, can be used to produce LAOS. The SHOP process employs a combination of oligomerization and olefin metathesis chemistries to produce a variety of LAOs using a Ni-based catalyst. INEOS, a global manufacturer of petrochemicals has also developed a proprietary process for synthesizing a wide range of LAOs with the flexibility to change distributions of products to meet demand.

The demand for short chain alpha olefins, such as 1-octene and 1-hexene, has been rising as well. Specific chain length ranges of alpha-olefins are crucial for specific applications. For example, short chain-lengths (e.g., 1-butene to 1-octene) are used to improve the rheological melt and solid resin properties of polyethylene. The main consumer of 1-octene is the high-volume production of linear low-density polyethylene (LLDPE) and high-density polyethylene (HDPE), which expands each year. Co-monomer alpha-olefin content is 1-2% for HDPE grades and reaches up to 30% for some LLDPE grades.

As such, 1-octene is a very important chemical feedstock that is in market demand. Aside from the processes discussed above, various catalysts have been developed for the tetramerization of ethylene to form 1-octene. However, these catalysts have deficiencies in several respects. As such, improved catalysts, which are suitable for tetramerization of ethylene to from 1-octene, are desired in the industry.

SUMMARY

Fouling, as described herein, refers to the undesirable formation of polymers. Such polymers may form as side-products in the reaction of ethylene to form 1-octene when a catalyst system including chromium is used. However, as described herein, it has been discovered that the utilization of a co-catalyst that is a reaction product of an antifouling compound and an organoaluminum compound, may reduce fouling. As described herein, such antifouling compounds may include quaternary salts, chlorinated hydrocarbons, and esters, and it is believed that the incorporation of such antifouling compounds into the catalyst system may be responsible for reduced fouling. Moreover, in some embodiments, the utilization of the co-catalyst described herein may contribute to maintaining the selectivity of 1-octene, or even enhancing the selectivity of 1-octene, as compared with similar catalyst systems that do not include the antifouling compound.

According to one or more embodiments, a catalyst system suitable for tetramerizing ethylene to form 1-octene may include a catalyst comprising a reaction product of a chromium compound and a ligand having the structure according to Formula (II).

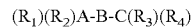

$$(R_1)(R_2)A\text{-}B\text{-}C(R_3)(R_4) \qquad (II)$$

In Formula (II), A and C may be independently chosen from phosphorus, arsenic, antimony, bismuth, and nitrogen; B may be a linking group between A and C; and $R_1$, $R_2$, $R_3$, and $R_4$ may be independently chosen from a $(C_1\text{-}C_{50})$ hydrocarbyl or a $(C_1\text{-}C_{50})$ heterohydrocarbyl. The catalyst system may comprise a co-catalyst comprising a reaction product of an organoaluminum compound and an antifouling compound. The antifouling compound may comprise one or more quaternary salts; one or more organic acids, organic acid salts, esters, anhydrides, or combinations of these; one or more chlorinated hydrocarbons, chloro-aluminum alkyls, or combinations of these; one or more polyether alcohols; or one or more non-polymeric ethers.

Additional features and advantages of the described embodiments will be set forth in the detailed description which follows, and in part will be readily apparent to those skilled in the art from that description or recognized by practicing the described embodiments, including the detailed description which follows, as well as the claims.

DETAILED DESCRIPTION

Described herein are catalysts systems, which may be utilized to produce 1-octene from ethylene by tetramerization. Also described herein are methods for utilizing such catalyst systems. The presently described catalyst systems may include a catalyst and a co-catalyst, as are described in detail herein. In one or more embodiments described herein, the catalyst may comprise chromium and, in some embodiments, may be the reaction product of a chromium compound and a ligand. The co-catalyst may be the reaction product of at least an antifouling compound and an organoaluminum compound.

In one or more embodiments, the catalyst systems described herein may be used to selectively oligomerize ethylene to produce 1-octene, while reducing undesirable polymerization, sometimes referred to in this disclosure as "fouling." For example, reactor fouling may occur at least partially due to the formation of solid polyethylene-based residues, which may reduce fluid flow and/or fully block or at least partially block fluids in a reactor system from flowing at a desired rate. Without being bound by any particular theory, it is believed that the incorporation of the antifouling compound into the catalyst system reduces fouling.

It should be understood that the catalyst systems presently described may not completely eliminate fouling during a reaction. However, in one or more embodiments, these catalyst systems reduce fouling as compared with catalyst systems which do not include the antifouling compound as described in the present disclosure. Also, it should be understood that, while the catalyst systems of the present disclosure may be useful in ethylene oligomerization reactions, such as ethylene dimerization to form 1-butene, they may also be useful for the catalysis of other chemical reactions, and the catalyst systems described in this disclosure should not be considered limited in their use to the tetramerization of ethylene to form 1-octene. It should further be understood that the antifouling agents described in this disclosure may be incorporated with other catalyst systems which contain, for example, non-chromium based catalysts.

As used in this disclosure, a "catalyst" refers to any substance that increases the rate of a specific chemical reaction. Catalysts described in this disclosure may be utilized to promote various reactions, such as, but not limited to, tetramerization of ethylene to form 1-octene. Catalysts are generally not consumed in a reaction, but as would be understood in the art, may have reduced catalytic activity over time and need to be replaced and/or regenerated.

As used in this disclosure, a "co-catalyst" generally refers to any substance or chemical agent that brings about catalyst in conjunction with one or more catalysts. In some embodiments, a catalyst may have independent catalytic functionality, while in other embodiments, the catalyst may only have substantial catalytic functionality when paired with a co-catalyst. It should be understood that the catalyst and co-catalyst may be, in some embodiments, bonded or formed in a complex, but in other embodiments are not bonded or present in a complex. Some co-catalysts may be said to "activate" a catalyst, which may increase catalytic functionality.

Additionally, as used in this disclosure, a "catalyst system" refers to any catalytically functional collection of chemical species. In some embodiments, a catalyst system may include a catalyst and a co-catalyst. In additional embodiments, a catalyst system may include additional components, such as, for example, additional co-catalysts or non-catalytic additives which may serve other purposes.

As described herein, a "reaction product" refers to a chemical species formed from the reaction of any two or more reactant species. A reaction product may result in a covalent or ionic bond, coordination, or other interaction between reactant species. In some embodiments, two or more reaction products may result from the reaction of the reactant species, and all of these possible produced chemical species are included in the reactant product as described herein.

When used to describe certain carbon atom-containing chemical groups, a parenthetical expression having the form "$(C_x-C_y)$" means that the unsubstituted form of the chemical group has from x carbon atoms to y carbon atoms, inclusive of x and y. For example, a $(C_1-C_{50})$ alkyl group is an alkyl group having from 1 to 50 carbon atoms in its unsubstituted form. In some embodiments and general structures, certain chemical groups may be substituted by one or more substituents. A substituted chemical group defined using the "$(C_x-C_y)$" parenthetical may contain more than y carbon atoms depending on the identity of any substituents. For example, a "$(C_1-C_{50})$ alkyl substituted with exactly one phenyl ($—C_6H_5$)" may contain from 7 to 56 carbon atoms. Thus, in general when a chemical group defined using the "$(C_x-C_y)$" parenthetical is substituted by one or more carbon atom-containing substituents, the minimum and maximum total number of carbon atoms of the chemical group is determined by adding to both x and y the combined sum of the number of carbon atoms from all of the carbon atom-containing substituents.

The term "substitution" means that at least one hydrogen atom ($—H$) bonded to a carbon atom or heteroatom of a corresponding unsubstituted compound or functional group is replaced by a substituent. Substituents may be any suitable functional group or radical that could replace a hydrogen atom bonded to a carbon atom or heteroatom of a corresponding unsubstituted compound. For example, substituents may include, but are not limited to, hydrocarbyls, cyclohydrocarbyls, aryls, halogens, and amines.

The term "$—H$" means a hydrogen or hydrogen radical that is covalently bonded to another atom. "Hydrogen" and "$—H$" are interchangeable, and unless clearly specified have identical meanings.

The term "hydrocarbyl" means a monovalent radical resulting from removal of any hydrogen atom from a hydrocarbon, including aromatic hydrocarbons, non-aromatic hydrocarbons, cyclic or acyclic hydrocarbons, saturated or unsaturated hydrocarbons, straight chain or branched chain hydrocarbons, and substituted or unsubstituted hydrocarbons.

The term "heterohydrocarbyl" refers to a hydrocarbyl, from which at least one carbon atom has been replaced with a heteroatom. Examples of heteroatoms include, without limitation, oxygen, nitrogen, sulfur, and phosphorus.

The term "cyclohydrocarbyl" means an aromatic or non-aromatic, cyclic hydrocarbyl having at least three carbon atoms, including monocyclic and polycyclic hydrocarbyls, fused and non-fused polycyclic hydrocarbyls, and bicyclic hydrocarbyls, non-aromatic saturated or unsaturated cyclic hydrocarbyls, and substituted or unsubstituted hydrocarbyls.

The term "aryl" means an aromatic hydrocarbon radical, in which the carbon atoms of the aromatic system may be substituted or unsubstituted. Aryls include monocyclic, bicyclic and tricyclic aromatic hydrocarbon radicals. A monocyclic aromatic hydrocarbon radical includes one aromatic ring; a bicyclic aromatic hydrocarbon radical has two rings; and a tricyclic aromatic hydrocarbon radical has three rings. When the bicyclic or tricyclic aromatic hydrocarbon radical is present, at least one of the rings of the radical is aromatic. The other ring or rings of the aromatic radical may be independently fused or non-fused and aromatic or non-aromatic. Non-limiting examples of aryls include phenyl; fluorenyl; tetrahydrofluorenyl; indacenyl; hexahydroindacenyl; indenyl; dihydroindenyl; naphthyl; tetrahydronaphthyl; and phenanthrenyl.

The term "alkyl" means a saturated hydrocarbon radical that may be linear or branched. Accordingly, the term "$(C_1-C_{20})$ alkyl" means a saturated linear or branched hydrocarbon radical of from 1 to 20 carbon atoms that is unsubstituted or substituted. Examples of unsubstituted ($C_1-C_{20}$) alkyl include methyl; ethyl; 1-propyl; 2-propyl; 1-butyl; 2-butyl; 2-methylpropyl; 1,1-dimethylethyl; 1-pentyl; 1-hexyl; 1-heptyl; 1-nonyl; and 1-decyl. Examples of substituted ($C_1$-$C_{20}$) alkyl include trifluoromethyl and trifluoroethyl.

The term "saturated" means lacking carbon-carbon double bonds, carbon-carbon triple bonds, and (in heteroatom-containing groups) carbon-nitrogen, carbon-phosphorous, and carbon-silicon double bonds. Where a saturated chemical group is substituted by one or more substituents, one or more double and/or triple bonds optionally may be present in substituents. The term "unsaturated" means containing one or more carbon-carbon double bonds or carbon-carbon triple bonds, or (in heteroatom-containing groups) one or more carbon-nitrogen double bonds, carbon-phosphorous double bonds, or carbon-silicon double bonds, not including double bonds that may be present in substituents, if any, or in aromatic rings or heteroaromatic rings, if any.

In one or more embodiments, the catalyst comprises chromium. It should be understood that, as contemplated herein, the catalyst may be any chemical compound that includes chromium that is catalytically functional for, without limitation, promoting the selective tetramorization of ethylene to from 1-octene.

In one or more embodiments, the catalyst includes a reaction product of a chromium compound and a ligand. It should be understood that the chromium complexes described herein, which may coordinate with ligands, are not necessarily limited in structure, but includes chromium. In one or more embodiments, the chromium compound includes an organic chromium salt, an inorganic chromium salt, a chromium complex, or combinations of these. In some embodiments, the chromium compound includes chromium trichloride tris-tetrahydrofuran complex, (benzene)tricarbonyl chromium, chromium (III) octanoate, chromium (III) acetylacetonate, chromium hexacarbonyl, chromium (III) 2-ethylhexanoate, or combinations of these.

It should be understood that the ligands described herein, which may coordinate with chromium of the chromium complex are not necessarily limited in structure. However, in some embodiments, the ligand may have a structure according to formula (I):

$(R)_n A\text{-}B\text{-}C(R)_m$        (I)

In formula (I), A and C are independently chosen from phosphorus (P), arsenic (As), antimony (Sb), oxygen (O), bismuth (Bi), sulfur (S), selenium (Se), or nitrogen (N); B is a linking group between A and C; each R is independently chosen from any ($C_1$-$C_{50}$) homo-hydrocarbyl or ($C_1$-$C_{50}$) hetero-hydrocarbyl group, where at least one R group may be substituted with a polar substituent; and n and m are determined by the respective valence and oxidation state of A and C. In some embodiments, A and C of the ligand of formula (I) may function as electron donors for coordination with the chromium compound. As described herein, an "electron donor" refers to any chemical substituent that donates electron used in chemical (including dative covalent) bond formation.

In one or more embodiments, the ligand may have a structure according to formula (II):

$(R_1)(R_2)A\text{-}B\text{-}C(R_3)(R_4)$        (II)

In formula (II), A and C are independently chosen from phosphorus (P), arsenic (As), antimony (Sb), bismuth (Bi), or nitrogen (N); B is a linking group between A and C; $R_1$, $R_2$, $R_3$, and $R_4$ are independently chosen from any ($C_1$-$C_{50}$) hydrocarbyl. In one or more embodiments, at least one of $R_1$, $R_2$, $R_3$, and $R_4$ may be substituted with a polar substituent. In one or more embodiments, the ($C_1$-$C_{50}$) hydrocarbyl group may be a ($C_1$-$C_{50}$) homo-hydrocarbyl or ($C_1$-$C_{50}$) hetero-hydrocarbyl group. As described herein, a "polar substituent" refers to any chemical substituent with a permanent electric dipole moment, as defined by the IUPAC. Example polar substituents include methoxy, ethoxy, isopropoxy, ($C_3$-$C_{20}$)alkoxy, phenoxy, pentafluorophenoxy, trimethylsiloxy, dimethylamino, methylsulfanyl, tosyl, methoxymethy, methylthiomethyl, 1,3-oxazolyl, methomethoxy, hydroxyl, amino, phosphino, arsino, stibino, sulphate, and nitro.

In some embodiments, up to four of $R_1$, $R_2$, $R_3$, and $R_4$ may have substituents on the atom adjacent to the atom bound to A or C. In some embodiments, each of $R_1$, $R_2$, $R_3$, and $R_4$ may be aromatic, including heteroaromatic, and are substituted by any substituent on an atom adjacent to the atom bound to A or C. In some embodiments, not more than two of $R_1$, $R_2$, $R_3$, and $R_4$, if they are aromatic, may have substituents on the atom adjacent to the atom bound to A or C. In some embodiments, any polar substituents on $R_1$, $R_2$, $R_3$, and $R_4$, if they are aromatic, are not on the atom adjacent to the atom bound to A or C. For example, at least one of $R_1$, $R_2$, $R_3$, and $R_4$, if aromatic, may be substituted with a polar substituent on the $2^{nd}$ or further atom from the atom bound to A or C. In some embodiments, any polar substituent on one or more of $R_1$, $R_2$, $R_3$, and $R_4$ may be electron donating. In some embodiments, any of the groups $R_1$, $R_2$, $R_3$, and $R_4$ may independently be linked to one or more of each other or to the linking group B to form a cyclic structure together with A and C, A and B or B and C. In some embodiments, $R_1$, $R_2$, $R_3$, and $R_4$ may be independently chosen from a benzyl, phenyl, tolyl, xylyl, mesityl, biphenyl, naphthyl, anthracenyl, methoxy, ethoxy, phenoxy, tolyloxy, dimethylamino, diethylamino, methylethylamino, thiophenyl, pyridyl, thioethyl, thiophenoxy, trimethylsilyl, dimethylhydrazyl, methyl, ethyl, ethenyl, propyl, butyl, propenyl, propynyl, cyclopentyl, cyclohexyl, ferrocenyl, or tetrahydrofuranyl group.

In some embodiments, A and/or C may be independently oxidized by S, Se, N or O, where the valence of A and/or C allows for such oxidation. For example, A and C may be independently phosphorus or phosphorus oxidized by S or Se or N or O.

In some embodiments, B may be an organic linking group comprising a ($C_1$-$C_{50}$) hydrocarbyl, a ($C_1$-$C_{50}$) substituted hydrocarbyl, a ($C_1$-$C_{50}$) heterohydrocarbyl, and a ($C_1$-$C_{50}$) substituted heterohydrocarbyl; an inorganic linking group comprising single atom links; ionic links; and a group comprising methylene, dimethylmethylene, 1,2-ethane, 1,2-phenylene, 1,2-propane, 1,2-catechol, 1,2-dimethylhydrazine, —B($R_5$)—, —Si($R_5$)$_2$—, —P($R_5$)— and —N($R_5$)—, where $R_5$ is hydrogen, a ($C_1$-$C_{50}$) hydrocarbyl or a ($C_1$-$C_{50}$) substituted hydrocarbyl, a ($C_1$-$C_{50}$) substituted heteroatom or a halogen. For example, B may be —N($R_5$)—, where $R_5$ is a ($C_1$-$C_{50}$) hydrocarbyl or a ($C_1$-$C_{50}$) substituted hydrocarbyl group. $R_5$ may be hydrogen or may be selected from the groups consisting of alkyl, substituted alkyl, aryl, substituted aryl, aryloxy, substituted aryloxy, halogen, nitro, alkoxycarbonyl, carbonyloxy, alkoxy, aminocarbonyl, carbonylamino, dialkylamino, silyl groups or derivatives thereof, and aryl substituted with any of these substituents. For example, $R_5$ may be an isopropyl, a 1-cyclohexylethyl, a 2-methylcyclohexyl, or a 2-octyl group. In some embodiments, B may be a single atom spacer. As described herein, a "single atom linking spacer" refers to a substituted or non-substituted atom that is bound directly to A and C. In one or more embodiments, B is not bound to a second ligand, such as a second PNP ligand.

Without intending to be bound by theory, the electronic properties of the ligand, whether moieties of the ligand are electron donors or electron withdrawers affect the binding strength of ethylene to the catalytic metal center. Additionally, the bulkiness of the ligand may introduce steric hindrances which also may affect the binding strength of ethylene to the metal center. Accordingly, the ligand may affect the reactivity and selectivity of the catalyst toward the formation of 1-octene.

The chromium compound and the ligand may be produced using procedures and methods known in the art. For example, procedures and methods for producing the chromium compound and the ligand are described in U.S. Pat. No. 7,297,832, which is incorporated by reference in its entirety.

As described herein, the catalyst system also includes a co-catalyst. In the embodiments described herein, the co-catalyst may be the reaction product of an organoaluminum compound and the antifouling compound. It should be understood that the organoaluminum compound may comprise multiple chemical species, or a single chemical species. For example, in one or more embodiments, the co-catalyst may comprise a reaction product of the antifouling compound and methylaluminoxane. In one or more embodiments, the co-catalyst may comprises a reaction product of the antifouling compound, methylaluminoxane, and an alkyl aluminum compound. Likewise, the antifouling compound may comprise multiple chemical species, or a single chemical species.

In one or more embodiments, the co-catalyst may be formed from an organoaluminum compound. As described herein, an "organoaluminum compound" refers to any chemical compound that includes at least one aluminum atom and any organic moiety. It should be appreciated that the organoaluminum compound may include several chemical species, or may be a single chemical species.

In some embodiments, the organoaluminum complex may be an alkyl aluminum compound. The aluminum alkyl compounds described herein may have a generalized structure shown in formula (III):

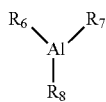

Formula (III)

where $R_6$, $R_7$ and $R_8$ may each be a hydrogen atom or a ($C_1$-$C_{20}$) hydrocarbyl group an oxygen-containing moiety, or a halide. In embodiments, the ($C_1$-$C_{20}$) hydrocarbyl group may be a substituted or unsubstituted ($C_1$-$C_{20}$) linear or branched hydrocarbyl group. In one or more embodiments, $R_3$, $R_4$, and $R_5$ may each be a hydrogen or a linear or branched ($C_1$-$C_{20}$) alkyl group. In additional embodiments, the alkyl aluminum compound may be an aluminoxane structure (i.e., a partial hydrolysate of trialkylaluminum compounds). For example, and not by way of limitation, suitable aluminum alkyl compounds may include trimethylaluminium, triethylaluminum, tripropylaluminum, tri-isobutylaluminum, diisobutyialuminium hydride, trihexylaluminum, tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, methylaluminoxane (MAO), ethylaluminoxane (EAO), and modified alkylaluminoxanes, such as modified methylaluminoxane (MMAO). As described herein, a "modified alkylaluminoxane" refers to a alkylaluminoxane that includes one or more modifier groups, such as isobuytyl or n-octyl groups in addition to the alkyl groups. In one or more embodiments, the organoaluminum compound of the catalyst system may comprise, consist essentially of, or consist of any of these compounds.

Without intending to be bound by theory, the alky aluminum compound may be operable to remove impurities, or poisons that may have a negative effect on the catalyst. Additionally, the alkyl aluminum compound may be operable to alkylate the chromium complex. Furthermore, the alkyl aluminum compound may be operable to activate the chromium complex to allow the coordination of the ethylene with the catalyst.

In one or more embodiments, the co-catalyst may be formed from an antifouling compound. As described herein, an "antifouling compound" refers to any chemical compound that decreases fouling by polymer production. It should be appreciated that the antifouling compound may include several chemical species, or may be a single chemical species.

In some embodiments, the antifouling compound may be a quaternary salt. As described herein, a "quaternary salt" refers to any salt including a quaternary compound. As described herein, a "quaternary compound" refers to any cation that includes a central positively charged atom with four substituents. The quaternary salts described herein may have a generalized structure shown in formula (IV):

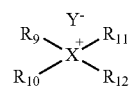

Formula (IV)

In formula (IV), X is a nonmetal element from Group 15 or Group 16 of the International Union of Pure and Applied Chemistry periodic table of the elements (IUPAC periodic table); Y is an anion; and $R_9$, $R_{10}$, $R_{11}$, and $R_{12}$ are independently chosen from hydrogen or a ($C_1$-$O_{50}$) hydrocarbyl group. In one or more embodiments, the ($C_1$-$C_{50}$) hydrocarbyl group may be a substituted or unsubstituted ($C_1$-$C_{50}$) linear or branched hydrocarbyl group. In one or more embodiments, $R_9$, $R_{10}$, $R_{11}$, and $R_{12}$ are each independently chose from a hydrogen, an alkyl group, or an aryl group. In some embodiments, X is nitrogen (N), phosphorus (P), arsenic (As), or sulfur (S). In embodiments where X is nitrogen, the quaternary salt may be an ammonium salt. In embodiments where X is phosphorus, the quaternary salt may be a phosphonium salt. In embodiments, where X is sulfur, the quaternary salt may be a sulfonium salt. In some embodiments, Y is a halogen, a carbonate, a nitrate, a sulfate, a phosphate, or a sulphonate. For example, the quaternary salt of formula (IV) may include nitrogen as X and bromine as Y (i.e., the quaternary salt of formula (IV) may a quaternary ammonium salt).

Without being bound by any particular theory, it is believed that the reaction between the organoaluminum compound and the antifouling compound may produce various chemical compounds. That is, the co-catalyst may include one or more chemical compounds, each of which are reaction products of the organoaluminum compound and the antifouling compound. In embodiments wherein the organoaluminum compound is the aluminum alkyl compound of formula (VI) and the antifouling compound is the quaternary salt of formula (VII), the reaction product of the organoaluminum compound and the antifouling compound may be a quaternary salt including a quaternary compound as the cation and an aluminum compound as the anion. An example reaction of the aluminum alkyl compound of formula (III) and a quaternary salt of formula (IV) is shown in reaction scheme (I):

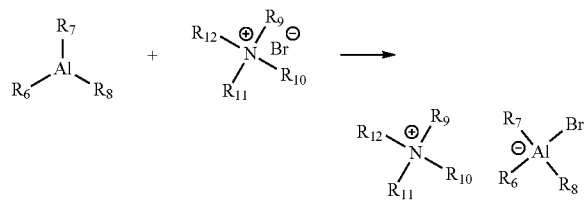

In some embodiments, the antifouling compound may be an organic acid, a derivative of an organic acid, or combinations of these. As described herein, a "derivative of an organic acid" refers to any chemical compound derived from the organic acid. For example, derivatives of an organic acid may be a salt of the organic acid, an ester derived from the organic acid, an anhydride derived from the organic acid, or combinations of these. The organic acids described herein may have a generalized structure shown in formula (V):

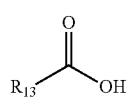

Formula (V)

The organic acid salts described herein may have a generalized structure shown in formula (VI):

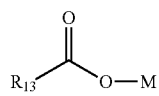

Formula (VI)

The esters described herein may have a generalized structure shown in formula (VII):

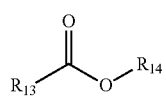

Formula (VII)

The anhydrides described herein may have a generalized structure shown in formula (VIII):

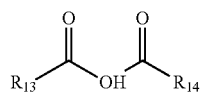

Formula (VIII)

In formulas (V)-(VIII), $R_{13}$ and $R_{14}$ are independently chosen from an unsubstituted hydrocarbyl group or a substituted hydrocarbyl group; and M is an element from Group 1 or Group 2 of the International Union of Pure and Applied Chemistry periodic table of the elements (IUPAC periodic table).

Without being bound by any particular theory, it is believed that the reaction between the organoaluminum compound and the antifouling compound may produce various chemical compounds. An example reaction of the aluminum alkyl compound of formula (III) and the ester of formula (VII) is shown in reaction scheme (II):

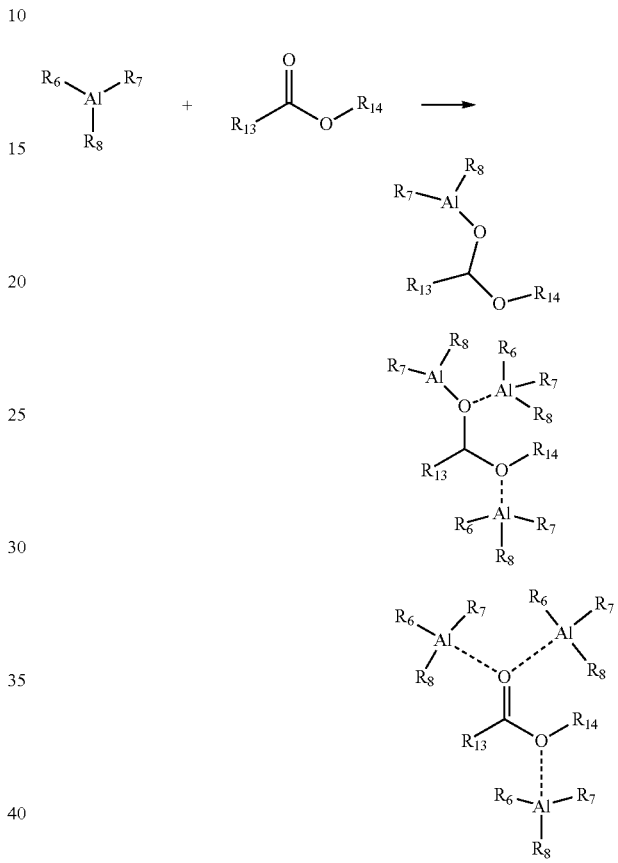

In some embodiments, the antifouling compound may be a chlorinated hydrocarbon, a chloro-aluminum alkyl, or combinations of these. As described herein, a "chlorinated hydrocarbon" refers to any organic chemical compound that includes at least one covalently bonded atom of chlorine that has an effect on the chemical behavior on the organic chemical compound. For example, a chlorinated hydrocarbon may be a chloroalkane (i.e., an alkane with one or more hydrogens substituted by chlorine). The chloro-aluminum alkyls described herein may have a generalized structure shown in formula (IX):

Formula (IX)

$R_{15}$
  \
   Al—Cl
  /
$R_{16}$

In formula (IX), $R_{15}$ and $R_{16}$ are independently chosen from an unsubstituted hydrocarbyl group or a substituted hydrocarbyl group. In some embodiments, the antifouling compound is hexachloroethane ($C_2Cl_6$).

Without being bound by any particular theory, it is believed that the reaction between the organoaluminum compound and the antifouling compound may produce various chemical compounds. An example reaction of the aluminum alkyl compound of formula (III) and the chloroaluminum alkyl of formula (IX) is shown in reaction scheme (III):

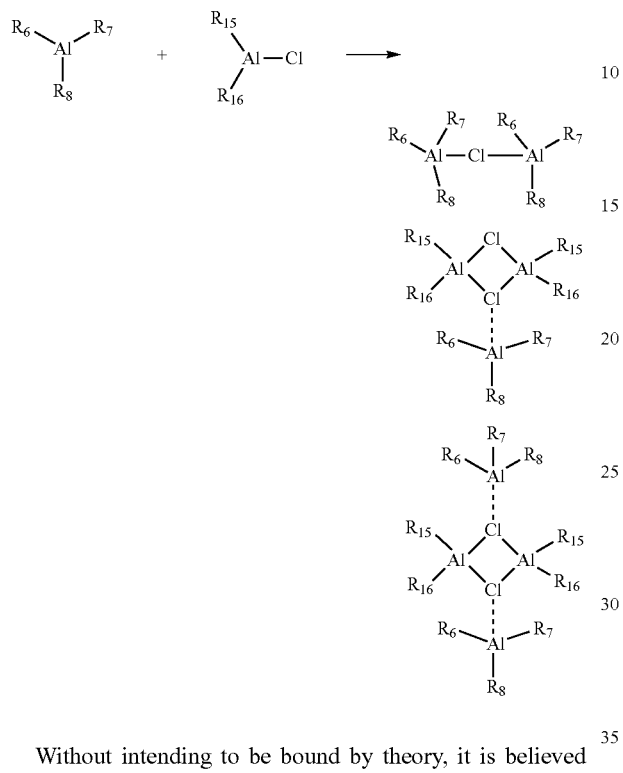

Without intending to be bound by theory, it is believed that the chloride of the chlorinated hydrocarbon may coordinate with a vacant coordination site on the metal center such that the formation of 1-octene may be favored and the formation of polymeric by-products may be disfavored.

In one or more embodiments, the antifouling compound may be a polyether alcohol. In some embodiments, the polyether alcohol may include monomer units comprising one or more carbon chains separating ether moieties. For example, the polyether alcohols described herein may have a generalized structure shown in formula (X):

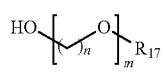

Formula (X)

In formula (X), $R_{17}$ is chosen from an unsubstituted hydrocarbyl group or a substituted hydrocarbyl group; m is an integer of from 1 to 100; and n is an integer from 1 to 20. In some embodiments, $R_{17}$ nay be an unsubstituted hydrocarbyl group that includes at least 1 carbon atom, at least 2 carbon atoms, at least 3 carbon atoms, at least 4 carbon atoms, at least 5 carbon atoms, at least 6 carbon atoms, at least 7 carbon atoms, at least 8 carbon atoms, at least 8 carbon atoms, at least 9 carbon atoms, at least 10 carbon atoms, at least 11 carbon atoms, or at least 12 carbon atoms. In some embodiment, m is an integer of from 1 to 75, from 1 to 50, from 1 to 25, from 25 to 100, from 25 to 75, from 25 to 50, from 50 to 100, from 50 to 75, or from 75 to 100. In some embodiments, n is an integer of from 1 to 15, from 1 to 10, from 1 to 5, from 5 to 20, from 5 to 15, from 5 to 10, from 10 to 20, from 10 to 15, or from 15 to 20.

Without being bound by any particular theory, it is believed that the reaction between the organoaluminum compound and the antifouling compound may produce various chemical compounds. An example reaction of the aluminum alkyl compound of formula (III) and the polyether alcohol of formula (X) is shown in reaction scheme (IV):

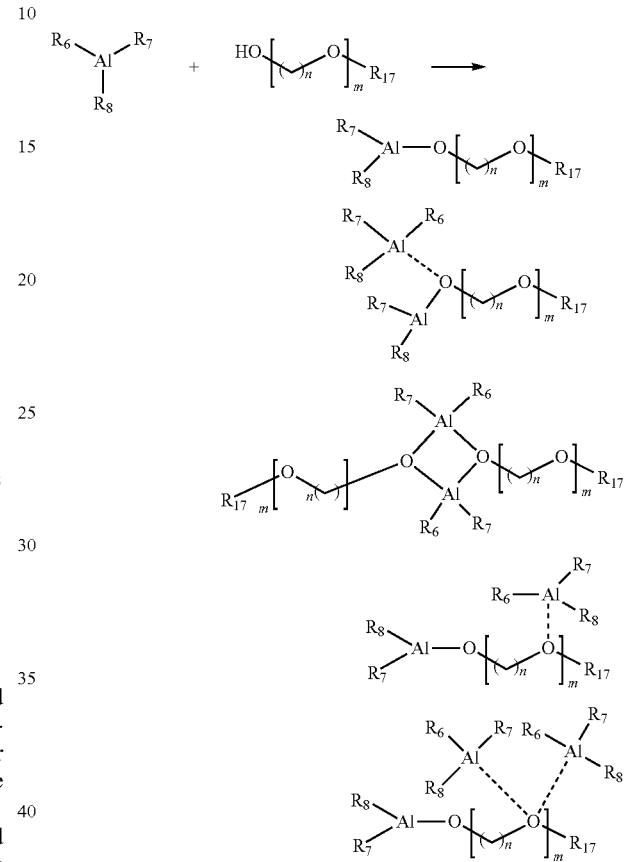

In some embodiments, the antifouling compound may include one or more non-polymeric ethers. The non-polymeric ethers may include cyclic non-polymeric ethers such as, but not limited to, tetrahydrofuran (TIP), a dioxane, a tetrahydropyran (THP), or combinations of these. As described herein, a "non-polymeric" ethers refers to any chemical compound that includes one or more ethers but do not include long ether polymer chains. Generally, such non-polymeric ethers comprise one or two ether moieties, and comprise less than 10 ether moieties.

Without intending to be bound by theory, the reaction products of the organoaluminum compound and the antifouling compound may function as a surfactant and affect the ion-pair of the metal activation center of the catalyst. This may affect the coordination of ethylene with the metal activation center and the degree of chain-transfer predominant with respect to chain propagation. By controlling the chain propagation, the reaction products of the organoaluminum compound and the antifouling compound may increase the product selectivity of 1-octene and reduce the production of large polymers, resulting in reduced fouling. Furthermore, it is contemplated that in one or more embodiments the reactions between the quaternary salt and the organoaluminum compound are relatively fast and that there are little to no free quaternary salts remaining in the catalytic system once the quaternary salt and organoaluminum compound react.

It should be understood that the co-catalysts contemplated herein may include a number of different chemical species. However, as described in embodiments herein, these co-catalyst species share certain structures and can be commonly classified by moiety or structure.

In one or more embodiments described herein, the antifouling compound and organoaluminum complex may have a molar ratio of from 0.001 to 1, such as from 0.01 to 0.1. For example, according to embodiments, the molar ratio of antifouling compound to organoaluminum complex may be from 0.001 to 0.01, from 0.01 to 0.02, from 0.02 to 0.03, from 0.03 to 0.04, from 0.04 to 0.05, from 0.05 to 0.06, from 0.06 to 0.07, from 0.07 to 0.08, from 0.08 to 0.09, from 0.09 to 0.1, from 0.1, to 0.2, from 0.2 to 0.3, from 0.3 to 0.4, from 0.4 to 0.5, from 0.5 to 0.6, from 0.6 to 0.7, from 0.7 to 0.8, from 0.8 to 0.9, from 0.9 to 1, or any combination of these ranges, such as any subgroup encompassed by any combination of these ranges.

According to one or more embodiments, the catalyst system may further comprise additional co-catalysts and/or additives. It should be understood that these additional co-catalysts and/or additives are optional and are not included in all embodiments described herein. Examples of additional co-catalysts and/or additives include, without limitation, any of the organoaluminium compounds described herein which form the co-catalyst (e.g. diisobutylaluminium hydride or and TEAL) could also be added to the catalyst system. Such additional co-catalysts may be present if an excess amount of organoaluminum compound is added to form the co-catalyst, such that all antifouling complex is reacted by excess organoaluminum compound remains in the solution.

In one or more embodiments, ethylene may be contacted with the catalyst system described herein to from a product comprising 1-octene. Contacting may generally include any mixing, combining, etc. of the reactant ethylene with the catalyst system. In one or more embodiments, the catalyst and co-catalyst may be separately prepared, and then combined, prior to contacting of the catalyst system with ethylene. In one or more embodiments, the ethylene may be contacted with the catalyst system in the presence of hydrogen.

The reaction may be performed as a batch reaction or as a continuous process reaction, such as a continuous stir tank reactor process. According to further embodiments, the pressure of the reactor may be from 5 bar to 120 bar (such as from 20 bar to 60 bar), and the reactor temperature may be from 25 ° C. to 180 ° C. (such as from 30 ° C. to 120 ° C.). However, process conditions outside of these ranges are contemplated, especially in view of the specific design of the reactor system and concentrations of the reactants and catalysts.

It should be understood that, in one or more embodiments, similar or identical catalyst systems which do not include the antifouling compound may exhibit increased fouling. In one or more embodiments, the introduction of the antifouling agent into a catalyst system may suppress polymer formation while not greatly reducing catalytic activity of 1-octene formation. In one embodiment, polymer formation (fouling) may be reduced by at least 5%, 10%, 20%, 30%, 40%, 50%, 60%, 70%, 80%, 90%, or even 95% by the inclusion of an antifouling compound. In one embodiment, 1-octene production may be increased, stay the same, or may decrease by less than or equal to 50%, 40%, 30%, 20%, 10% or even 5% by the inclusion of an antifouling compound. In some embodiments, antifouling, compounds may both reduce the polymer formation (such as by at least 5%, 10%, 20%, 30%, 40%, 50%, 60%, 70%, 80%, 90% or even 95%) and increase, not effect, or decrease 1-octene production rate by less than or equal to 50%, 40%, 30%, 20%, 10% or even 5%. Reduction in polymer formation rates and catalytic activity on a percentage basis are based on catalyst systems which are formed from the antifouling compounds described herein as compared with catalyst systems which are void of an antifouling compound.

EXAMPLES

The various aspects of the present disclosure will be further clarified by the following examples. The examples are illustrative in nature and should not be understood to limit the subject matter of the present disclosure.

Catalyst Production Method

In the following examples, the catalyst was produced by dissolving 0.86 milligrams (mg) of Cr(acac)$_3$ and 1.07 mg of N,N-bis(diphenylphosphino)isopropylamine (Chemical Abstracts Service (CAS) No. 60981-68-2) in 100 milliliters (ml) of anhydrous methylcyclohexane (MCH) in an inert and moisture-free environment, and mixing for 30 minutes to produce a catalyst solution.

Co-Catalyst Production Method

In the following examples, the co-catalyst was produced by mixing 480 mg of MMAO-3A (CAS No. 146905-79-5) in heptane (7 wt. % aluminum) and an antifouling compound (AFC) such that the molar ratio of the AFC to aluminum (AFC:Al) was from 0.001 to 1 or from 0.01 to 0.1.

Ethylene Tetramerization Procedure

In the following examples, an ethylene tetramerization process (also referred to as a run) was conducted using the same general procedure. Each run was conducted in a 250 milliliter (ml) autoclave reactor unit. Before each run, the autoclave reactor unit was vacuum purged with ultrapure nitrogen to remove oxygen and moisture, which may be detrimental to the ethylene tetramerization reaction, and then filled with a desired amount of anhydrous MCH as a solvent. Once the autoclave reactor unit was prepared, the catalyst solution and co-catalyst, as described previously, were separately injected into the autoclave reactor unit such that the molar ratio of the co-catalyst to the catalyst (Co-Cat:Cat) was approximately 0.1. Subsequently, approximately 3 bar of ultrapure molecular hydrogen was charged to the autoclave reactor unit, which was then heated to a temperature of 45° C. In order to initiate the run, 45 bar of ethylene was charged to the autoclave rector unit. Once a desired run time of 60 min. was reached, the run was terminated by injecting 2.0 ml of methanol into the autoclave reactor unit, which was then depressurized. Any solid polymer produced was collected from the autoclave reactor unit, filtered, dried overnight in an oven at 110° C., and weighed.

Example 1

In Example 1, an ethylene tetramerization process, as described previously, was conducted using an AFC having a structure according to formula (XI):

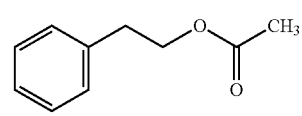

Formula (XI)

The results of Example 1 are reported in Table 1.

Example 2

In Example 2, an ethylene tetramerization process, as described previously, was conducted using an AFC having a structure according to formula (XII):

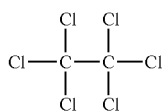

Formula (XII)

The results of Example 2 are reported in Table 1.

Example 3

In Example 3, an ethylene tetramerization process, as described previously, was conducted using an AFC having a structure according to formula (XIII):

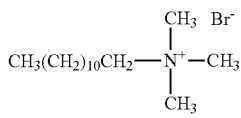

Formula (XIII)

The results of Example 3 are reported in Table 1.

Comparative Example 4

In Comparative Example 4, an ethylene tetramerization process, as described previously, was conducted in a manner similar to Examples 1-3, but no AFC was used (i.e., the solution of MMAO-3A in heptane was injected alone). The results of Comparative Example 4 are reported in Table 1.

TABLE 1

| Example | $Cr(acac)_3$ (mmol) | PNP (mmol) | Al (mmol) | Molar Ratio (Co-Cat:Cat) | Activity (mol 1-octene/mol catalyst/hour) | 1-Hexene (mol. %) | 1-Octene (mol. %) | Polymer (wt. %) |
|---|---|---|---|---|---|---|---|---|
| Example 1 | 0.0025 | 0.0025 | 1.25 | 0.1 | 124,630 | 9.52 | 74.09 | 5.73 |
| Example 2 | 0.0025 | 0.0025 | 1.25 | 0.1 | 113,180 | 9.88 | 74.65 | 6.14 |
| Example 3 | 0.0025 | 0.0025 | 1.25 | 0.1 | 100,292 | 9.23 | 74.47 | 5.71 |
| Comparative Example 4 | 0.0025 | 0.0025 | 1.25 | — | 102,580 | 10.21 | 74.82 | 8.42 |

Reaction Conditions-Temperature: 45° C.; $C_2H_4$ Pressure: 45 bar; $H_2$ Pressure: 3 bar; Run Time: 60 min As shown in Table 1, the catalyst systems of Examples 1-3 each resulted in lower production of polymer than the catalyst system of Comparative Example 4. Accordingly, the catalyst systems of Examples 1-3 provide a benefit over the catalyst system of Comparative Example 4 by providing a relatively low polymer selectivity. Furthermore, the catalyst systems of Examples 1-3 generally provided comparable activity and selectivity for 1-octene to the catalyst system of Comparative Example 4, even surpassing the activity for 1-octene of the catalyst system of Comparative Example 4 in some cases.

In a first aspect of the present disclosure, a catalyst system suitable for tetramerizing ethylene to form 1-octene may include a catalyst comprising a reaction product of a chromium compound and a ligand having the structure according to Formula (II). In Formula (II), A and C may be independently chosen from phosphorus, arsenic, antimony, bismuth, and nitrogen; B may be a linking group between A and C; and $R_1$, $R_2$, $R_3$, and $R_4$ may be independently chosen from a $(C_1-C_{50})$ hydrocarbyl or a $(C_1-C_{50})$ heterohydrocarbyl. The catalyst system may comprise a co-catalyst comprising a reaction product of an organoaluminum compound and an antifouling compound. The antifouling compound may comprise one or more quaternary salts; one or more organic acids, organic acid salts, esters, anhydrides, or combinations of these; one or more chlorinated hydrocarbons, chloro-aluminum alkyls, or combinations of these; one or more polyether alcohols; or one or more non-polymeric ethers.

A second aspect of the present disclosure may include the first aspect, where the antifouling compound comprises one or more quaternary salts.

A third aspect of the present disclosure may include either the first or second aspect, where the antifouling compound comprises one or more organic acids.

A fourth aspect of the present disclosure may include any of the first through third aspects, where the antifouling compound comprises one or more organic acid salts.

A fifth aspect of the present disclosure may include any of the first through fourth aspects, where the antifouling compound comprises one or more esters.

A sixth aspect of the present disclosure may include any of the first through fifth aspects, where the antifouling compound comprises one or more anhydrides.

A seventh aspect of the present disclosure may include any of the first through sixth aspects, where the antifouling compound comprises one or more chlorinated hydrocarbons.

An eighth aspect of the present disclosure may include any of the first through seventh aspects, where the antifouling compound comprises one or more chloro-aluminum alkyls.

A ninth aspect of the present disclosure may include any of the first through eighth aspects, where the antifouling compound comprises one or more polyether alcohols.

A tenth aspect of the present disclosure may include any of the first through ninth aspects, where the antifouling compound comprises one or more non-polymeric ethers.

An eleventh aspect of the present disclosure may include any of the first through tenth aspects, where the chromium compound comprises one or more of an organic chromium salt, an inorganic chromium salt, and a chromium complex.

A twelfth aspect of the present disclosure may include any of the first through eleventh aspects, where the chromium compound comprises one or more of chromium trichloride tris-tetrahydrofuran complex, (benzene)tricarbonyl chromium, chromium (III) octanoate, chromium (III) acetylacetonoate, chromium hexacarbonyl, and chromium (III) 2-ethylhexanoate.

A thirteenth aspect of the present disclosure may include any of the first through twelfth aspects, where the organoaluminum compound has the structure according to formula (III) in which $R_6$, $R_7$, and $R_8$ are each selected from a hydrogen atom and a $(C_1\text{-}C_{20})$ hydrocarbyl group.

A fourteenth aspect of the present disclosure may include any of the first through thirteenth aspects, where the organoaluminum compound comprises one or more of trimethylaluminium, triethylaluminum, tripropylaluminum, tri-isobutylaluminum, diisobutylaluminium hydride, trihexylaluminum, tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, methylaluminoxane (MAO), ethylaluminoxane (EAO), and modified methylaluminoxane (MMAO).

A fifteenth aspect of the present disclosure may include any of the first through fourteenth aspects, where the co-catalyst comprises a reaction product of the antifouling compound and methylaluminoxane.

A sixteenth aspect of the present disclosure may include any of the first through fourteenth aspects, where the co-catalyst comprises a reaction product of the antifouling compound, methylaluminoxane, and an alkyl aluminum compound.

A seventeenth aspect of the present disclosure may include any of the first through sixteenth aspects, where the molar ratio of the antifouling compound to the organoaluminum complex is from 0.001 to 1.

According to an eighteenth aspect of the present disclosure, a method for tetramerizing ethylene to form 1-octene may comprise contacting ethylene with a catalyst system of any of the first through sixteenth aspects to form a product comprising 1-octene.

A nineteenth aspect of the present disclosure may include the eighteenth aspect, where ethylene is formed in conditions of a reactor pressure from 5 bar to 120 bar; and a reactor temperature from 25° C. to 180° C.

The subject matter of the present disclosure has been described in detail and by reference to specific embodiments. It should be understood that any detailed description of a component or feature of an embodiment does not necessarily imply that the component or feature is essential to the particular embodiment or to any other embodiment. Further, it should be apparent to those skilled in the art that various modifications and variations can be made to the described embodiments without departing from the spirit and scope of the claimed subject matter.

For the purposes of describing and defining the present disclosure it is noted that the terms "about" or "approximately" are utilized in this disclosure to represent the inherent degree of uncertainty that may be attributed to any quantitative comparison, value, measurement, or other representation. The terms "about" and/or "approximately" are also utilized in this disclosure to represent the degree by which a quantitative representation may vary from a stated reference without resulting in a change in the basic function of the subject matter at issue.

It is noted that one or more of the following claims utilize the term "wherein" as a transitional phrase. For the purposes of defining the present technology, it is noted that this term is introduced in the claims as an open-ended transitional phrase that is used to introduce a recitation of a series of characteristics of the structure and should be interpreted in like manner as the more commonly used open-ended preamble term "comprising."

It should be understood that where a first component is described as "comprising" a second component, it is contemplated that, in some embodiments, the first component "consists" or "consists essentially of" that second component. It should further be understood that where a first component is described as "comprising" a second component, it is contemplated that, in some embodiments, the first component comprises at least 10%, at least 20%, at least 30%, at least 40%, at least 50%, at least 60%, at least 70%, at least 80%, at least 90%, at least 95%, or even at least 99% that second component (where % can be weight % or molar %).

Additionally, the term "consisting essentially of" is used in this disclosure to refer to quantitative values that do not materially affect the basic and novel characteristic(s) of the disclosure. For example, a chemical composition "consisting essentially" of a particular chemical constituent or group of chemical constituents should be understood to mean that the composition includes at least about 99.5% of a that particular chemical constituent or group of chemical constituents.

It should be understood that any two quantitative values assigned to a property may constitute a range of that property, and all combinations of ranges formed from all stated quantitative values of a given property are contemplated in this disclosure. It should be appreciated that compositional ranges of a chemical constituent in a composition should be appreciated as containing, in some embodiments, a mixture of isomers of that constituent. In additional embodiments, the chemical compounds may be present in alternative forms such as derivatives, salts, hydroxides, etc.

What is claimed is:

1. A catalyst system suitable for tetramerizing ethylene to form 1-octene, the catalyst system comprising:
    a catalyst comprising a reaction product of a chromium compound and a ligand having the structure:

wherein:
        A and C are independently chosen from phosphorus, arsenic, antimony, bismuth, and nitrogen;
        B is a linking group between A and C;
        $R_1$, $R_2$, $R_3$, and $R_4$ are independently chosen from a $(C_1\text{-}C_{50})$ hydrocarbyl or a $(C_1\text{-}C_{50})$ heterohydrocarbyl; and
    a co-catalyst comprising a reaction product of an organoaluminum compound and an antifouling compound, wherein the antifouling compound comprises:
        one or more quaternary salts;
        one or more organic acids, organic acid salts, esters, anhydrides, or combinations of these;
        one or more chlorinated hydrocarbons, chloro-aluminum alkyls, or combinations of these;
        one or more polyether alcohols; or
        one or more non-polymeric ethers.

2. The catalyst system of claim 1, wherein the antifouling compound comprises one or more quaternary salts.

3. The catalyst system of claim 1, wherein the antifouling compound comprises one or more organic acids.

4. The catalyst system of claim 1, wherein the antifouling compound comprises one or more organic acid salts.

5. The catalyst system of claim 1, wherein the antifouling compound comprises one or more esters.

6. The catalyst system of claim 1, wherein the antifouling compound comprises one or more anhydrides.

7. The catalyst system of claim 1, wherein the antifouling compound comprises one or more chlorinated hydrocarbons.

8. The catalyst system of claim 1, wherein the antifouling compound comprises one or more chloro-aluminum alkyls.

9. The catalyst system of claim 1, wherein the antifouling compound comprises one or more polyether alcohols.

10. The catalyst system of claim 1, wherein the antifouling compound comprises one or more non-polymeric ethers.

11. The catalyst system of claim 1, wherein the chromium compound comprises one or more of an organic chromium salt, an inorganic chromium salt, and a chromium complex.

12. The catalyst system of claim 1, wherein the chromium compound comprises one or more of chromium trichloride tris-tetrahydrofuran complex, (benzene)tricarbonyl chromium, chromium (III) octanoate, chromium (III) acetylacetonoate, chromium hexacarbonyl, and chromium (III) 2-ethylhexanoate.

13. The catalyst system of claim 1, wherein the organoaluminum compound has the structure:

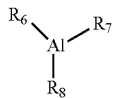

wherein $R_6$, $R_7$, and $R_8$ are each selected from a hydrogen atom and a ($C_1$-$C_{20}$) hydrocarbyl group.

14. The catalyst system of claim 1, wherein the organoaluminum compound comprises one or more of trimethylaluminium, triethylaluminum, tripropylaluminum, tri-isobutylaluminum, diisobutylaluminium hydride, trihexylaluminum, tri-n-octylaluminium, methylaluminium dichloride, ethylaluminium dichloride, dimethylaluminium chloride, diethylaluminium chloride, aluminium isopropoxide, ethylaluminiumsesquichloride, methylaluminiumsesquichloride, methylaluminoxane (MAO), ethylaluminoxane (EAO), and modified methylaluminoxane (MMAO).

15. The catalyst system of claim 1, wherein the co-catalyst comprises a reaction product of the antifouling compound and methylaluminoxane.

16. The catalyst system of claim 1, wherein the co-catalyst comprises a reaction product of the antifouling compound, methylaluminoxane, and an alkyl aluminum compound.

17. The catalyst system of claim 1, wherein the molar ratio of the antifouling compound to the organoaluminum complex is from 0.001 to 1.

18. A method for tetramerizing ethylene to form 1-octene, the method comprising contacting ethylene with a catalyst system of any of claim 1 to form a product comprising 1-octene.

19. The method of claim 18, wherein the ethylene is formed in the conditions of:
a reactor pressure from 5 bar to 120 bar; and
a reactor temperature from 25° C. to 180° C.

* * * * *